US007184837B2

(12) United States Patent
Goetz (10) Patent No.: US 7,184,837 B2
(45) Date of Patent: Feb. 27, 2007

(54) SELECTION OF NEUROSTIMULATOR PARAMETER CONFIGURATIONS USING BAYESIAN NETWORKS

(75) Inventor: Steven M. Goetz, Brooklyn Center, MN (US)

(73) Assignee: Medtronic, Inc., Minneapolis, MN (US)

( * ) Notice: Subject to any disclaimer, the term of this patent is extended or adjusted under 35 U.S.C. 154(b) by 568 days.

(21) Appl. No.: 10/767,674

(22) Filed: Jan. 29, 2004

(65) Prior Publication Data

US 2005/0060008 A1 Mar. 17, 2005

Related U.S. Application Data

(60) Provisional application No. 60/503,220, filed on Sep. 15, 2003.

(51) Int. Cl.
*A61N 1/36* (2006.01)

(52) U.S. Cl. ............... 607/45; 607/2; 607/27; 607/30; 607/59; 128/925

(58) Field of Classification Search .......... 607/59, 607/2, 27, 45, 62; 128/920, 923, 924, 925
See application file for complete search history.

(56) References Cited

U.S. PATENT DOCUMENTS

| 4,872,122 | A | 10/1989 | Altschuler et al. |
| 4,895,574 | A | 1/1990 | Rosenberg |
| 5,005,143 | A | 4/1991 | Altschuler et al. |
| 5,240,009 | A | 8/1993 | Williams |
| 5,280,792 | A | 1/1994 | Leong et al. |
| 5,358,513 | A | 10/1994 | Powell, III et al. |
| 5,383,910 | A | 1/1995 | den Dulk |
| 5,443,486 | A | 8/1995 | Hrdlicka et al. |
| 5,522,863 | A | 6/1996 | Spano et al. |
| 5,626,140 | A | 5/1997 | Feldman et al. |
| 5,645,069 | A | 7/1997 | Lee |
| 5,673,367 | A | 9/1997 | Buckley |
| 5,702,429 | A | 12/1997 | King |

(Continued)

FOREIGN PATENT DOCUMENTS

EP 0 653 224 A2 5/1995

(Continued)

OTHER PUBLICATIONS

International Preliminary Report on Patentability, dated Jun. 3, 2005 for International Patent Application PCT/US2004/030017, filed Sep. 14, 2004 (9 pgs.).

*Primary Examiner*—Kennedy Schaetzle
(74) *Attorney, Agent, or Firm*—Shumaker & Sieffert, P.A (57) ABSTRACT

In general, the invention is directed to a technique for selection of parameter configurations for an implantable neurostimulator using Bayesian networks. The technique may be employed by a programming device to allow a clinician to select parameter configurations, including electrode configurations, and then program an implantable neurostimulator to deliver therapy using the selected parameter configurations. In operation, the programming device executes a parameter configuration search algorithm to guide the clinician in the selection of parameter configurations. The search algorithm relies on a Bayesian network structure that encodes conditional probabilities describing different states of the parameter set. The Bayesian network structure provides a conditional probability table that represents causal relationships between different parameter configurations. The search algorithm uses the Bayesian network structure to infer likely efficacies of possible parameter configurations based on the efficacies of parameter configurations already observed.

51 Claims, 9 Drawing Sheets

U.S. PATENT DOCUMENTS

| | | | |
|---|---|---|---|
| 5,706,403 | A | 1/1998 | Shibata et al. |
| 5,713,932 | A | 2/1998 | Gillberg et al. |
| 5,716,382 | A | 2/1998 | Snell |
| 5,774,357 | A | 6/1998 | Hoffberg et al. |
| 5,782,885 | A | 7/1998 | Andersson |
| 5,788,645 | A | 8/1998 | Swanson et al. |
| 5,810,014 | A | 9/1998 | Davis et al. |
| 5,867,386 | A | 2/1999 | Hoffberg et al. |
| 5,875,108 | A | 2/1999 | Hoffberg et al. |
| 5,901,246 | A | 5/1999 | Hoffberg et al. |
| 5,903,454 | A | 5/1999 | Hoffberg et al. |
| 5,920,477 | A | 7/1999 | Hoffberg et al. |
| 5,921,937 | A | 7/1999 | Davis et al. |
| 5,938,688 | A | 8/1999 | Schiff |
| 5,954,754 | A * | 9/1999 | Stoop et al. .................. 607/28 |
| 5,995,868 | A | 11/1999 | Dorfmeister et al. |
| 5,999,854 | A | 12/1999 | Deno et al. |
| 6,081,750 | A | 6/2000 | Hoffberg et al. |
| 6,129,745 | A | 10/2000 | Sun et al. |
| 6,171,239 | B1 | 1/2001 | Humphrey |
| 6,192,273 | B1 | 2/2001 | Igel et al. |
| 6,263,230 | B1 | 7/2001 | Haynor et al. |
| 6,263,238 | B1 | 7/2001 | Brewer et al. |
| 6,269,267 | B1 | 7/2001 | Bardy et al. |
| 6,345,200 | B1 | 2/2002 | Mouchawar et al. |
| 6,370,423 | B1 | 4/2002 | Guerrero et al. |
| 6,385,479 | B1 | 5/2002 | Sibbitt et al. |
| 6,386,882 | B1 | 5/2002 | Linberg |
| 6,400,996 | B1 | 6/2002 | Hoffberg et al. |
| 6,408,290 | B1 | 6/2002 | Thiesson et al. |
| 6,418,424 | B1 | 7/2002 | Hoffberg et al. |
| 6,434,261 | B1 | 8/2002 | Zhang et al. |
| 6,456,622 | B1 | 9/2002 | Skaanning et al. |
| 6,473,653 | B1 | 10/2002 | Schallhorn et al. |
| 6,480,743 | B1 | 11/2002 | Kirkpatrick et al. |
| 6,480,814 | B1 | 11/2002 | Levitan |
| 6,496,816 | B1 | 12/2002 | Thiesson et al. |
| 6,497,655 | B1 | 12/2002 | Linberg et al. |
| 6,505,075 | B1 | 1/2003 | Weiner |
| 6,522,928 | B2 | 2/2003 | Whitehurst et al. |
| 6,530,954 | B1 | 3/2003 | Eckmiller |
| 6,539,263 | B1 | 3/2003 | Schiff et al. |
| 6,547,746 | B1 | 4/2003 | Marino |
| 6,549,804 | B1 | 4/2003 | Osorio et al. |
| 6,554,762 | B2 | 4/2003 | Leysieffer |
| 6,556,699 | B2 | 4/2003 | Rogers et al. |
| 6,572,542 | B1 | 6/2003 | Houben et al. |
| 6,575,894 | B2 | 6/2003 | Leysieffer et al. |
| 6,597,943 | B2 | 7/2003 | Taha et al. |
| 6,609,017 | B1 | 8/2003 | Shenoy et al. |
| 6,658,287 | B1 | 12/2003 | Litt et al. |
| 6,659,968 | B1 | 12/2003 | McClure |
| 6,662,051 | B1 | 12/2003 | Eraker et al. |
| 6,697,672 | B2 | 2/2004 | Andersson |
| 6,704,595 | B2 | 3/2004 | Bardy |
| 2002/0016638 | A1 | 2/2002 | Mitra et al. |
| 2002/0016699 | A1 | 2/2002 | Hoggart et al. |
| 2002/0038294 | A1 | 3/2002 | Matsugu |
| 2002/0045804 | A1 | 4/2002 | Christopher et al. |
| 2002/0055779 | A1 | 5/2002 | Andrews |
| 2002/0087201 | A1 | 7/2002 | Firlik et al. |
| 2002/0091419 | A1 | 7/2002 | Firlik et al. |
| 2002/0099303 | A1 | 7/2002 | Bardy |
| 2002/0103512 | A1 | 8/2002 | Echauz et al. |
| 2002/0106709 | A1 | 8/2002 | Potts et al. |
| 2002/0123673 | A1 | 9/2002 | Webb et al. |
| 2002/0133198 | A1 | 9/2002 | Kramer et al. |
| 2002/0138013 | A1 | 9/2002 | Guerrero et al. |
| 2002/0143262 | A1 | 10/2002 | Bardy |
| 2002/0151992 | A1 | 10/2002 | Hoffberg et al. |
| 2002/0169367 | A1 | 11/2002 | Bardy |
| 2002/0169483 | A1 | 11/2002 | Henry et al. |
| 2002/0173727 | A1 | 11/2002 | Bardy |
| 2002/0198572 | A1 | 12/2002 | Weiner |
| 2003/0041866 | A1 | 3/2003 | Linberg et al. |
| 2003/0043815 | A1 | 3/2003 | Tinsley et al. |
| 2003/0050568 | A1 | 3/2003 | Green et al. |
| 2003/0053663 | A1 | 3/2003 | Chen et al. |
| 2003/0078522 | A1 | 4/2003 | Mitra et al. |
| 2003/0088274 | A1 | 5/2003 | Gliner et al. |
| 2003/0093129 | A1 | 5/2003 | Nicolelis et al. |
| 2003/0097159 | A1 | 5/2003 | Schiff et al. |
| 2003/0097161 | A1 | 5/2003 | Firlik et al. |
| 2003/0105409 | A1 | 6/2003 | Donoghue et al. |
| 2003/0158587 | A1 | 8/2003 | Esteller et al. |
| 2003/0195569 | A1 | 10/2003 | Swerdlow et al. |
| 2003/0216654 | A1 | 11/2003 | Xu et al. |
| 2004/0103001 | A1 | 5/2004 | Mazar et al. |
| 2004/0129271 | A1 | 7/2004 | Hickle |
| 2004/0158298 | A1 | 8/2004 | Gliner et al. |

FOREIGN PATENT DOCUMENTS

| | | |
|---|---|---|
| EP | 0 653 224 B1 | 5/1995 |
| EP | 0 541 338 | 9/1996 |
| EP | 0 756 877 | 2/1997 |
| EP | 0 796 636 | 9/1997 |
| EP | 0 684 858 | 4/1998 |
| EP | 0 848 965 A2 | 6/1998 |
| EP | 0 882 469 | 12/1998 |
| EP | 1 192 971 | 4/2002 |
| EP | 0 848 965 B1 | 8/2003 |
| EP | 0 653 224 | 1/2004 |
| WO | WO 00/10455 | 3/2000 |
| WO | WO 01/10455 | 3/2000 |
| WO | WO 01/17419 | 3/2001 |
| WO | WO 01/43823 | 6/2001 |
| WO | WO 0143635 | 6/2001 |
| WO | WO 01/56467 | 8/2001 |
| WO | WO 01/60445 | 8/2001 |
| WO | WO 01/82995 | 11/2001 |
| WO | WO 02/02622 | 1/2002 |
| WO | WO 02/15777 | 2/2002 |
| WO | WO 03/033070 | 4/2003 |
| WO | WO 03/037231 | 5/2003 |
| WO | WO 03/094721 | 11/2003 |
| WO | WO 04/031919 | 4/2004 |

* cited by examiner

|  | Iteration | | | | | | | | | |
|---|---|---|---|---|---|---|---|---|---|---|
|  | 1 | | 2 | | 3 | | 4 | | 5 | |
| Target | Yes | No | Yes | No | Yes | No | Yes | No | Yes | No |
| L0 | 0.50 | 0.50 | 0.50 | 0.50 | 0.50 | 0.50 | 0.50 | 0.50 | 0.50 | 0.50 |
| L1 | 0.50 | 0.50 | 0.50 | 0.50 | 0.50 | 0.50 | 0.50 | 0.50 | 0.50 | 0.50 |
| L2 | 0.50 | 0.50 | 0.50 | 0.50 | 0.50 | 0.50 | 0.50 | 0.50 | 0.50 | 0.50 |
| L3 | 0.10 | 0.90 | 0.10 | 0.90 | 0.11 | 0.89 | 0.11 | 0.89 | 0.12 | 0.88 |
| L4 | 0.00 | 1.00 | 0.00 | 1.00 | 0.00 | 1.00 | 0.00 | 1.00 | 0.00 | 1.00 |
| L5 | 0.10 | 0.90 | 0.10 | 0.90 | 0.11 | 0.89 | 0.11 | 0.89 | 0.07 | 0.93 |
| L6 | 0.50 | 0.50 | 0.50 | 0.50 | 0.50 | 0.50 | 0.50 | 0.50 | 0.05 | 0.95 |
| L7 | 0.50 | 0.50 | 0.50 | 0.50 | 0.50 | 0.50 | 0.50 | 0.50 | 0.38 | 0.62 |
| L8 | 0.50 | 0.50 | 0.50 | 0.50 | 0.50 | 0.50 | 0.50 | 0.50 | 0.50 | 0.50 |
| M0 | 0.50 | 0.50 | 0.50 | 0.50 | 0.50 | 0.50 | 0.50 | 0.50 | 0.50 | 0.50 |
| M1 | 0.50 | 0.50 | 0.50 | 0.50 | 0.50 | 0.50 | 0.50 | 0.50 | 0.50 | 0.50 |
| M2 | 0.50 | 0.50 | 0.50 | 0.50 | 0.50 | 0.50 | 0.50 | 0.50 | 0.50 | 0.50 |
| M3 | 0.13 | 0.87 | 0.13 | 0.87 | 0.13 | 0.87 | 0.13 | 0.87 | 0.13 | 0.87 |
| M4 | 0.00 | 1.00 | 0.00 | 1.00 | 0.00 | 1.00 | 0.00 | 1.00 | 0.00 | 1.00 |
| M5 | 0.13 | 0.87 | 0.15 | 0.85 | 0.08 | 0.92 | 0.07 | 0.93 | 0.06 | 0.94 |
| M6 | 0.50 | 0.50 | 0.50 | 0.50 | 0.54 | 0.46 | 0.71 | 0.29 | 0.13 | 0.87 |
| M7 | 0.50 | 0.50 | 0.50 | 0.50 | 0.50 | 0.50 | 0.53 | 0.47 | 0.51 | 0.49 |
| M8 | 0.50 | 0.50 | 0.50 | 0.50 | 0.50 | 0.50 | 0.50 | 0.50 | 0.50 | 0.50 |
| R0 | 0.50 | 0.50 | 0.50 | 0.50 | 0.50 | 0.50 | 0.50 | 0.50 | 0.50 | 0.50 |
| R1 | 0.50 | 0.50 | 0.50 | 0.50 | 0.50 | 0.50 | 0.50 | 0.50 | 0.50 | 0.50 |
| R2 | 0.50 | 0.50 | 0.50 | 0.50 | 0.50 | 0.50 | 0.50 | 0.50 | 0.50 | 0.50 |
| R3 | 0.50 | 0.50 | 0.54 | 0.46 | 0.51 | 0.49 | 0.53 | 0.47 | 0.50 | 0.50 |
| R4 | 0.50 | 0.50 | 0.27 | 0.73 | 0.30 | 0.70 | 0.31 | 0.69 | 0.27 | 0.73 |
| R5 | 0.50 | 0.50 | 0.60 | 0.40 | 0.64 | 0.36 | 0.60 | 0.40 | 0.75 | 0.25 |
| R6 | 0.50 | 0.50 | 0.50 | 0.50 | 0.54 | 0.46 | 0.71 | 0.29 | | |
| R7 | 0.50 | 0.50 | 0.50 | 0.50 | 0.50 | 0.50 | 0.53 | 0.47 | 0.55 | 0.45 |
| R8 | 0.50 | 0.50 | 0.50 | 0.50 | 0.50 | 0.50 | 0.50 | 0.50 | 0.50 | 0.50 |
| Evidence | LE34 = 1 | | RE34 = 3 | | RE45 = 4 | | RE56 = 5 | | LE56 = 2 | |

SELECTION OF NEUROSTIMULATOR PARAMETER CONFIGURATIONS USING BAYESIAN NETWORKS

TECHNICAL FIELD

This application claims the benefit of U.S. provisional application Ser. No. 60/503,220, filed Sep. 15, 2003, the entire content of which is incorporated herein by reference.

The invention relates to neurostimulation therapy and, more particularly, to techniques for selection of parameter configurations for an implantable neurostimulator.

BACKGROUND

Implantable medical devices are used to deliver neurostimulation therapy to patients to treat a variety of symptoms or conditions such as chronic pain, tremor, Parkinson's disease, epilepsy, incontinence, sexual dysfunction, or gastroparesis. The implantable medical device delivers neurostimulation therapy via one or more leads that include electrodes located proximate to the spinal cord, pelvic nerves, sacrum, or stomach, or within the brain of a patient. In general, the implantable medical device delivers neurostimulation therapy in the form of electrical pulses.

A clinician selects values for a number of programmable parameters in order to define a parameter configuration for the neurostimulation therapy to be delivered to a patient. For example, the clinician may select an amplitude, which may be a current or voltage amplitude, and pulse width for a stimulation waveform to be delivered to the patient, as well as a rate at which the pulses are to be delivered to the patient, and duration for which the stimulation energy is delivered. In addition, the clinician also selects particular electrodes within an electrode set to be used to deliver the pulses, and the polarities of the selected electrodes. The electrode combinations and polarities may be referred to as an electrode configuration. Hence, a parameter configuration may involve a variety of parameters including electrode configuration, amplitude, pulse width, pulse rate, and duration.

The process of selecting parameter configurations can be time consuming, and may require a great deal of trial and error before an optimum electrode configuration is discovered. The optimum parameter configuration may be better than other configurations in balancing clinical results and side effects experienced by the patient. This balance represents overall efficacy of an electrode configuration. The process for selecting parameter configurations can be difficult due to the combinatorial possibilities of parameters, the complexity of the underlying biophysics, and subjective and possibly inconsistent feedback from the patient concerning observed efficacy for a given parameter configuration.

SUMMARY

In general, the invention is directed to a technique for selection of parameter configurations for a neurostimulator using Bayesian networks. The technique may be employed by a programming device to allow a clinician to select parameter configurations, and then program an implantable neurostimulator to deliver therapy using the selected parameter configurations.

The parameter configurations may define electrode configurations, such as electrode combinations and polarities for an electrode set implanted in a patient. The electrode set may be carried by one or more implanted leads that are electrically coupled to the neurostimulator. In some embodiments, the parameter configurations may further define amplitudes, pulse widths, pulse rates, and durations of stimulation energy delivered by electrodes.

In operation, the programming device executes a parameter configuration search algorithm to guide the clinician in the selection of parameter configurations. For example, the search algorithm relies on a Bayesian network structure that encodes conditional probabilities describing different states of the parameter configuration. The Bayesian network structure provides a conditional probability table that represents causal relationships between different parameter configurations and clinical outcomes.

The search algorithm uses the Bayesian network structure to infer likely efficacies of possible parameter configurations based on the efficacies of parameter configurations already observed. The network structure can be learned from an existing set of data, or developed based on the input of a neurostimulation expert.

The Bayesian network structure may be updated based on new observations obtained for parameter configurations during the search. With the aid of the Bayesian network, a programming device provides a clinician with suggestions of which configurations are most likely to be efficacious given observations already obtained during the selection process. In general, efficacy refers to the balance between therapeutic benefit and undesirable side effects. As examples, efficacy can be observed by verbal feedback from the patient concerning therapeutic benefit and side effects, marking of a pain/parasthesia map, objective measurement using pain rating scales, quantification of side effects, a combination of the foregoing, or other observation techniques.

In one embodiment, the invention provides a method comprising selecting a first parameter configuration for a neurostimulator, observing efficacy of the first parameter configuration, and selecting a second parameter configuration for the neurostimulator based on the observed efficacy of the first parameter configuration and a Bayesian network structure relating additional parameter configurations according to probability of efficacy.

In another embodiment, the invention provides a computer-readable medium comprising instructions to cause a processor to select a first parameter configuration for a neurostimulator, observe efficacy of the first parameter configuration, and select a second parameter configuration for the neurostimulator based on the observed efficacy of the first parameter configuration and a Bayesian network structure relating additional parameter configurations according to probability of efficacy.

In an added embodiment, the invention provides a device comprising a processor programmed to select a first parameter configuration for a neurostimulator, observe efficacy of the first parameter configuration, and select a second parameter configuration for the neurostimulator based on the observed efficacy of the first parameter configuration and a Bayesian network structure relating additional parameter configurations according to probability of efficacy.

The invention may provide a number of advantages. For example, the invention may allow a clinician to more quickly identify desirable parameter configurations, reducing the overall amount of time the clinician spends programming neurostimulation therapy for a patient. In contrast to random or idiosyncratic search techniques, a technique based on Bayesian networks is capable of learning from the evaluation of earlier parameter configurations, and developing causal relationships that are more likely to lead to an optimum configuration. In general, the invention can reduce the length of a programming session for the clinician and the patient, and support selection of optimum parameter configurations to achieve overall efficacy. In addition, with the invention, it may be possible to identify optimal or near optimal parameter configurations that otherwise might not be identified by the clinician.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

FIG. 7 is a diagram of a sample search execution sequence for a Bayesian network structure as depicted in FIGS. 4–6.

DETAILED DESCRIPTION

Figure 1:
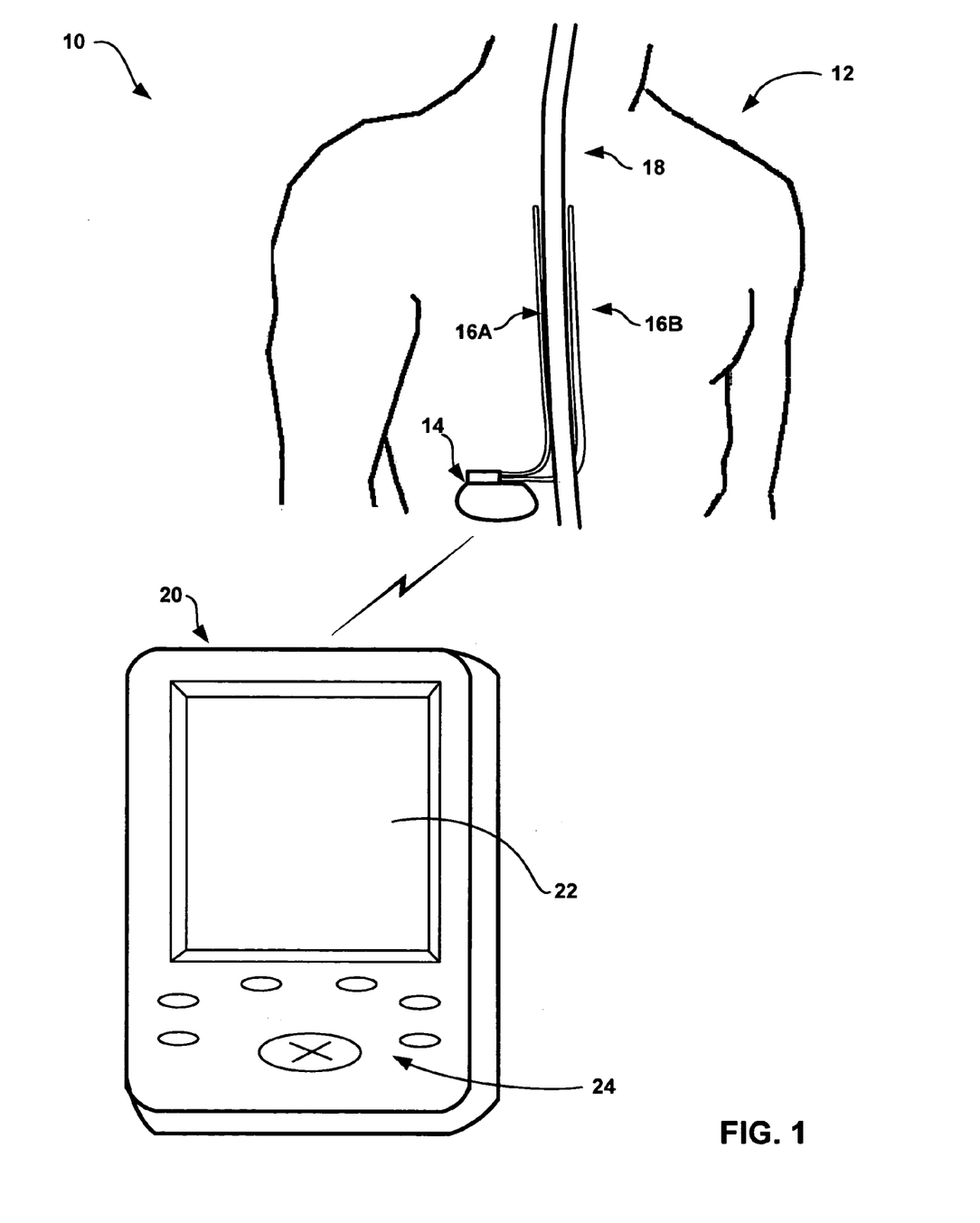
FIG. 1 is a diagram illustrating a system for programming and delivering neurostimulation therapy.

FIG. 1 is a diagram illustrating an example system 10 for programming neurostimulation therapy for and delivering neurostimulation therapy to a patient 12. System 10 includes an implantable medical device (IMD) 14 that delivers neurostimulation therapy to patient 12. IMD 14 may be an implantable pulse generator, and may deliver neurostimulation therapy to patient 12 in the form of electrical pulses. In accordance with the invention, system 10 makes use of Bayesian network structures for selection of parameter configurations, as will be described.

IMD 14 delivers neurostimulation therapy to patient 12 via leads 16A and 16B (collectively "leads 16"). Leads 16 may, as shown in FIG. 1, be implanted proximate to the spinal cord 18 of patient 12, and IMD 14 may deliver spinal cord stimulation (SCS) therapy to patient 12 in order to, for example, reduce pain experienced by patient 12. However, the invention is not limited to the configuration of leads 16 shown in FIG. 1 or the delivery of SCS therapy. For example, one or more leads 16 may extend from IMD 14 to the brain (not shown) of patient 12, and IMD 14 may deliver deep brain stimulation (DBS) therapy to patient 12 to, for example, treat tremor or epilepsy. As further examples, one or more leads 16 may be implanted proximate to the pelvic nerves (not shown), sacrum, or stomach (not shown), and IMD 14 may deliver neurostimulation therapy to treat incontinence, sexual dysfunction, or gastroparesis.

IMD 14 delivers neurostimulation therapy to patient 12 according to one or more neurostimulation therapy programs. A neurostimulation therapy program may include values for a number of parameters, and the parameter values define a parameter configuration for delivery of the neurostimulation therapy according to that program. In embodiments where IMD 14 delivers neurostimulation therapy in the form of electrical pulses, the parameters may include pulse voltage or current amplitudes, pulse widths, pulse rates, durations, and the like. Further, each of leads 16 includes electrodes (not shown in FIG. 1), and the parameters for a program may include information identifying which electrodes have been selected for delivery of pulses according to the program, and the polarities of the selected electrodes. Hence, a parameter configuration may involve a variety of parameters including electrode configuration, amplitude, pulse width, pulse rate, and duration. Although the invention may be applicable to neurostimulation parameter configuration in general, including configuration of parameters such as amplitude, pulse width, pulse rate, duration and electrode configuration, the invention will be described for purposes of illustration in the context of determining an electrode configuration.

A selected subset of the electrodes located on leads 16 and the polarities of the electrodes of the subset collectively define an "electrode configuration." The electrodes may be arranged in a standard inline lead configuration, or as a surgical paddle lead, grid, or other format. Electrode configurations refer to combinations of single or multiple cathode electrodes and single or multiple anode electrodes. Stimulation current flows between the cathodes and anodes for delivery of neurostimulation therapy. Hence, the polarities of the individual electrodes are another feature of the electrode configuration. Electrodes forming part of an electrode configuration may reside together on a single lead or on different leads.

System 10 also includes a programmer 20. Programmer 20 may, as shown in FIG. 1, be a handheld computing device. Programmer 20 includes a display 22, such as a liquid crystal display (LCD) or light emitting diode (LED) display, to display information to a user. Programmer 20 may also include a keypad 24, which may be used by a user to interact with programmer 20. In some embodiments, display 22 may be a touch screen display, and a user may interact with programmer 20 via display 22. A user may also interact with programmer 20 using peripheral pointing devices, such as a stylus or mouse. Keypad 24 may take the form of an alphanumeric keypad or a reduced set of keys associated with particular functions.

A clinician (not shown) may use programmer 20 to program neurostimulation therapy for patient 12. In particular, the clinician may use programmer 20 to create neurostimulation therapy programs. In some embodiments, programmer 20 may be used by the patient, e.g., over an extended trial screening process. As part of the program creation process, programmer 20 allows the clinician to identify parameter configurations that enable IMD 14 to deliver neurostimulation therapy that is desirable in terms of, for example, symptom relief, coverage area relative to symptom area, and side effects. Programmer 20 may also allow the clinician to identify parameter configurations that enable IMD 14 to deliver effective neurostimulation therapy with desirable device performance characteristics, e.g., low battery consumption. In addition, techniques as described herein may used to optimize therapy over the course of use of a chronically implanted IMD, e.g., by interaction between patient 12 and a patient programmer to record efficacy observations over time. In this case, a programmer carried by the patient may incorporate some or all of the functionality attributed to programmer 20 as described herein, including functionality designed to assist in identification of parameter configurations using Bayesian network structures.

Programmer 20 controls IMD 14 to test parameter configurations in order to allow a clinician to identify desirable parameter configurations in an efficient manner. As will be described in greater detail below, in some embodiments, programmer 20 selects electrode configurations to test based on an electrode configuration search algorithm, as described herein. In particular, according to such an algorithm, programmer 20 may first control IMD 14 to test one or more electrodes to identify a first electrode configuration, and then test other electrode configurations based on guidance built into the search algorithm.

Other neurostimulation parameters such as amplitude, pulse width, pulse rate, and duration also may be evaluated with the electrode configuration. For example, various parameters may be observed simultaneously with observation of each electrode configuration. Alternatively, once a smaller set of electrode configurations has been identified as providing efficacy for a given baseline set of amplitude, pulse width and pulse rate, then different amplitude, pulse width and pulse rate parameters may be iteratively observed for that smaller set of electrode configurations. Duration of the delivery of neurostimulation energy also may be observed. In this manner, amplitude, pulse width, and pulse rate parameters need not be evaluated for every electrode configuration, and especially those electrode configurations that do not present a high probability of efficacy as inferred from the Bayesian network structure.

By controlling IMD 14 to test parameter configurations in an intelligent manner, programmer 20 allows the clinician to more quickly identify desirable parameter configurations, reducing the overall amount of time the clinician spends programming neurostimulation therapy for patient 12. For example, in contrast to existing neurostimulation programming systems that present electrode configurations in a random order, or idiosyncratic search methodologies employed by clinicians, programmer 20 may select electrode configurations to test in a way that is more likely to enable desirable configurations to be selected earlier in the search. Consequently, the clinician may be able to end the search before all potential electrode combinations have been tested if one or more desirable configurations have already been identified, saving the amount of clinician and patient time required to achieve an efficacious electrode configuration. In addition, with the invention, it may be possible to identify optimal or near optimal parameter configurations that otherwise might not be identified by the clinician.

Even if the clinician elects to test all potential electrode combinations, e.g., if the electrode set is small enough to make testing all electrode configurations practical, programmer 20 may reduce the time required to identify desirable electrode configurations by automating selection of each new configuration to test. Additionally, programmer 20 may improve the search process by collecting efficacy information for each combination tested. As will be described in greater detail below, programmer 20 may present a list of electrode configurations to the clinician, ordered according to the efficacy information, allowing the clinician to more easily identify and select desirable configurations. This list of electrode configurations may be ordered and updated according to newly observed efficacy information as additional electrode configurations are evaluated. Similar techniques may be applied for other neurostimulation parameters forming part of a parameter configuration, such as amplitude, pulse width, pulse rate, and duration.

In order to control IMD 14 to test electrode configurations, programmer 20 may communicate with IMD 14 via telemetry techniques known in the art. For example, programmer 20 may communicate with IMD 14 via an RF telemetry head (not shown). Information identifying desirable combinations of electrodes identified by the clinician may be stored as part of parameter configurations associated neurostimulation therapy programs. Neurostimulation therapy programs created by the clinician using programmer 20 may be transmitted to IMD 14 via telemetry, and/or may be transmitted to another programmer (not shown), e.g., a patient programmer, that is used by patient 12 to control the delivery of neurostimulation therapy by IMD 14.

Figure 2:
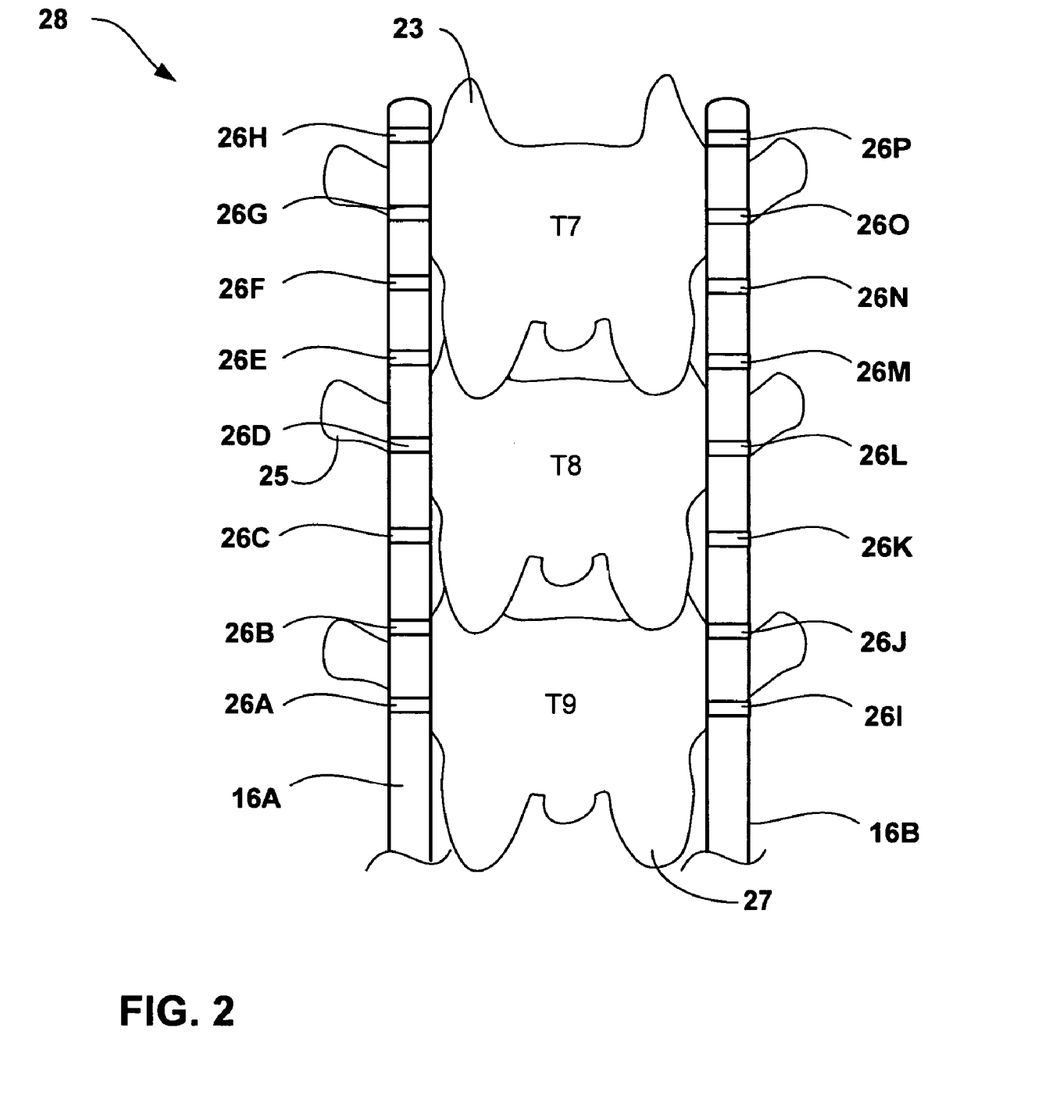
FIG. 2 is a diagram illustrating an example electrode set implanted proximate to the spine of a patient.

FIG. 2 is a block diagram illustrating an example configuration of leads 16. In the example configuration, lead 16A includes electrodes 26A–26H, and lead 16B includes electrodes 26I–26P. Hence, each lead 16 includes eight electrodes, although a lesser or greater number of electrodes are possible. Electrodes 26A–P (collectively "electrodes 26") may be ring electrodes. Electrodes 26 collectively form an electrode set 28 implanted within patient 12. As shown in FIG. 2, electrode set 28 includes eight electrodes on each of the two leads 16, which, as shown in FIG. 1, are implanted such that they are substantially parallel to each other and spinal cord 18 (FIG. 1), on substantially opposite sides of spinal cord 18, at approximately the same height relative to spinal cord 18, and oriented such that the distal ends of leads 16 are higher relative to the spinal cord than the proximal ends of leads 16. Therefore, the illustrated configuration of electrode set 28 may be described as a two-by-eight, side-by-side, upwardly oriented configuration. Of course, electrode set 28 is provided for purposes of example, and the invention may be applicable to other types of leads and electrode sets, including single lead electrode sets, flat paddle leads, grid arrays, and the like.

Such an electrode set is commonly used to provide SCS therapy. However, programmer 20 may be used to identify desirable combinations of electrodes within electrode sets that are configured in any way, and used to provide any type neurostimulation therapy. For example, a single lead including four or eight electrodes, two leads including four electrodes per lead, in-line leads, and offset leads, all of which may be oriented in any manner relative to patient 12, provide electrode set configurations that may be searched by programmer 20. In the example of FIG. 2, electrodes 26 are placed on opposite sides of the T7 vertebra 23, T8 vertebra 25 and T9 vertebra 27 of a human spine.

IMD 14 (FIG. 1) may deliver neurostimulation via any combination of electrodes 26. IMD 14 may independently activate each electrode 26 of set 28 to act as a cathode or anode for an electrode configuration, and each configuration will include at least one cathode and at least one anode. In some embodiments, it is possible that an electrode configuration may include a single electrode 26 acting as the cathode, with a can of IMD 14, i.e., the IMD housing, acting as the anode for the configuration.

In an electrode configuration, electrons flow from one or more electrodes acting as anodes for the configuration to one or more electrodes acting as cathodes for the configuration. The current between anodes and cathodes stimulates neurons between and proximate to the anodes and cathodes. Generally speaking, an electrode configuration enables desirable neurostimulation therapy when current is delivered in a direction and with an intensity sufficient to stimulate specific neurons or a sufficient number of specific neurons to alleviate a symptom without causing unacceptable side effects. Further, an electrode configuration enables desirable neurostimulation therapy when the symptom is alleviated without resorting to undesirably high pulse amplitudes.

As mentioned above, programmer 20 selects individual electrodes 26 or electrode configuration to test to allow a clinician to identify desirable electrode configuration according to an electrode search algorithm. Programmer 20 may select an appropriate search algorithm based on the configuration of electrode set 28, and may select electrodes 26 or electrode configurations based on the selected search algorithm. Programmer 20 controls IMD 14 to test a selected electrode 26 or electrode combination by controlling IMD 14 to deliver neurostimulation via the selected electrode 26 or combination.

In some embodiments, programmer 20 may first control IMD 14 to test one or more of electrodes 26 individually to identify the individual electrode or electrodes 26 which will act as a first cathode. In other embodiments, programmer 20 starts with a combination of selected electrodes 26. Generally, a clinician implants leads 16 in a location such that the center of electrode set 28 is proximate to an area that the clinician believes should be stimulated in order to alleviate symptoms. Therefore, programmer 20 may test electrodes 26 as the first cathode in an order such that electrodes 26 located centrally within electrode set 28, e.g., electrodes 26D–E and 26L–M illustrated in FIG. 2, are tested before peripherally located electrodes. If the clinician's estimation of the target region is inaccurate, programmer 20 will continue to test individual electrodes 26 in such an order until one of the electrodes 26 that enables desirable neurostimulation therapy when activated as the first cathode is identified. Initially locating a first cathode provides a "coarse" optimization of electrode combinations, allowing programmer 20 and the clinician to quickly identify the general area to which neurostimulation therapy should be delivered.

Programmer 20 may then control IMD 14 to test electrode configurations that include the first cathode. The various electrode configurations may be tested with a common set of stimulation parameters, such as a common voltage or current amplitude, frequency, and pulse width. In some embodiments, a series of different stimulation parameters may be applied for each combination of electrodes to test not only the efficacy of electrode combinations, but also electrode combinations with particular stimulation parameters such as amplitude, frequency and pulse width. Hence, an electrode configuration may apply to the combination of electrodes forming part of the neurostimulation parameter configuration, and the parameters associated with delivery of neurostimulation energy via the electrodes, such as amplitude, pulse width and pulse rate, may form another part of the parameter configuration.

Programmer 20 may control IMD 14 to try different ones of electrodes 26 as the first anode in a pair with the first cathode, and may add additional anodes and/or cathodes. In accordance with an embodiment of the invention, programmer 20 controls IMD 14 to test remaining electrodes 26 as first anodes, and additional anodes or cathodes, based on probability relationships represented by a Bayesian network structure. The Bayesian network structure may be employed by programmer 20 to allow a clinician to select electrode configurations, and then program IMD 14 to deliver therapy using the selected electrode configurations. The Bayesian network structure encodes conditional probabilities describing different states of electrode set 28. In particular, the Bayesian network structure provides a conditional probability table that represents causal relationships between different electrode configurations.

The search algorithm uses the Bayesian network structure to infer likely efficacies of possible parameter configurations, such as electrode configurations, based on the efficacies of parameter configurations already observed in the course of evaluation. The network structure can be learned from an existing set of data, or developed based on the input of a neurostimulation expert. The Bayesian network structure may be updated based on new observations obtained for parameter configurations during the search. With the aid of the Bayesian network, programmer 20 provides a clinician with suggestions of which electrode configurations are most likely to be efficacious given observations already obtained during the selection process. In response, the clinician may select the suggested electrode configurations next. In some cases, the selection of electrode configurations, or other parameters, may be automated in response to suggestions generated using the Bayesian network. In other cases, the selection of the parameter configurations may require human intervention from the clinician, but be aided by the suggestions.

Figure 3:
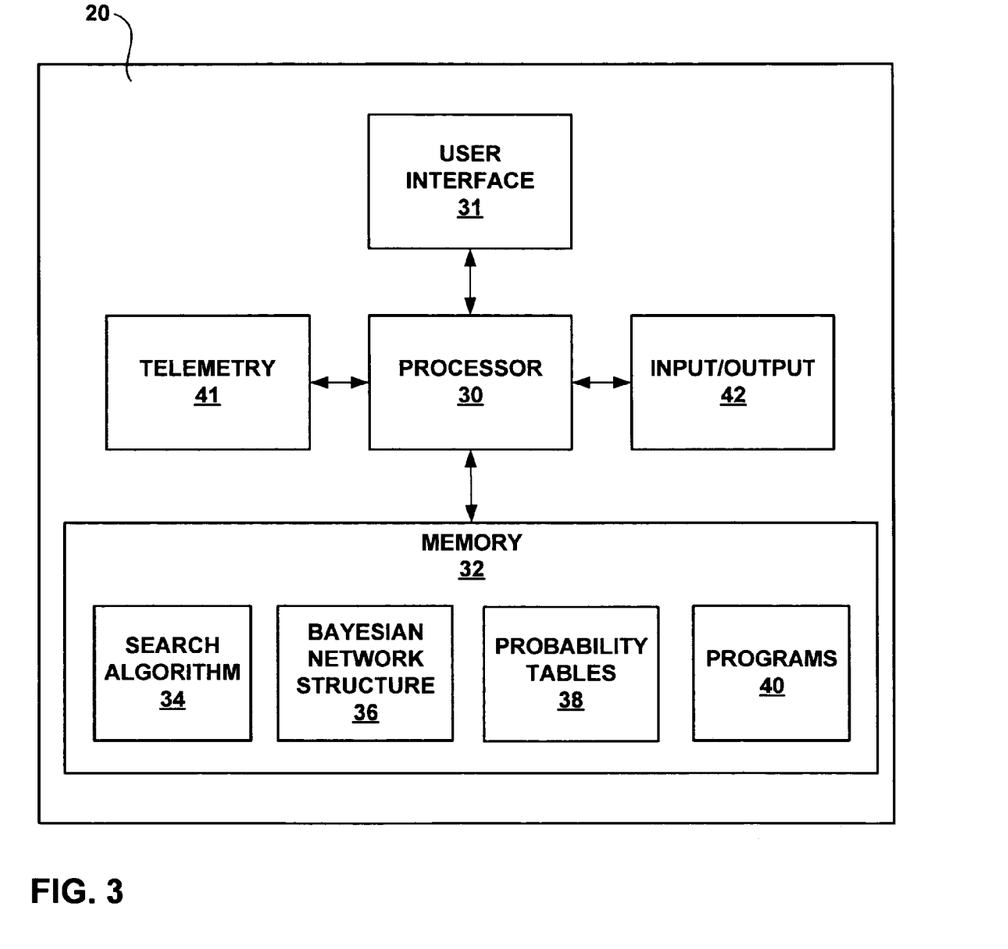
FIG. 3 is a block diagram illustrating a programming device used to identify desirable parameter combinations for neurostimulation therapy programs.

FIG. 3 is a block diagram illustrating an example configuration of programmer 20. A clinician or other user may interact with a processor 30 via a user interface 31 in order to identify and select electrode configurations as described herein. User interface 31 may include display 22 and keypad 24 (FIG. 1), and may also include a touch screen or peripheral pointing devices as described above. Processor 30 may also provide a graphical user interface (GUI) via user interface 31 to facilitate interaction with a user such as a clinician, technician, or other medical personnel. Processor 30 may include a microprocessor, a controller, a DSP, an ASIC, an FPGA, discrete logic circuitry, or the like.

Clinician programmer 20 also includes a memory 32. Memory 32 may include program instructions that, when executed by processor 30, cause clinician programmer 20 to perform the functions ascribed to clinician programmer 20 herein. For example, processor 30 may execute a parameter configuration search algorithm 34 stored within memory 32. In particular, processor 30 may execute an electrode configuration search algorithm to select individual electrodes 26 or electrode combinations to test to allow the clinician to identify desirable electrode combinations.

Search algorithm 34 executes based on the content of a Bayesian network structure 36, which encodes conditional probabilities describing different states of electrode set 28. In particular, Bayesian network structure 36 provides a conditional probability table 38 that represents causal relationships between different parameter configurations, such as electrode configurations. Hence, programmer 20 provides guidance to a clinician during the process of optimizing implantable device parameters. With Bayesian network structure 36, programmer 20 works by encoding conditional probabilities describing different states of electrode set 28 in a network structure. The Bayesian network structure 36 can then be used to infer the likely utilities of future electrode configurations based upon the efficacy, or other rating information, of those electrode configurations already observed.

For example, the causal relationships represented by the conditional probability table 38 of Bayesian network structure 36 provide an indication of which electrode configurations are likely to be efficacious when a related, but different, electrode configuration is found to be efficacious. The causal relationships may initially be determined by spatial position and proximity of individual electrodes relative to a stimulation target site and one another, but over time may be supplemented by causal information obtained by observing the actual efficacy of various electrode configurations.

As an illustration, an expert, such as a neurostimulation physician, may initially assign causal relationships based on his or her knowledge of typical relationships among electrode configurations. As actual electrode configurations are observed, however, the causal relationships may be supplemented with actual data. The actual data may be archived and used as the basis for a development of future Bayesian network structures.

In some embodiments, a plurality of different Bayesian network structures may be developed and devised for specific applications, such as different types of neurostimulation therapy, different symptomatic regimes, different electrode structures and device capabilities, and so forth. Hence, for selection of an electrode configuration, the user may first select a Bayesian network structure suitable for the present circumstances, and then use the network structure to guide the selection process.

As will be described in greater detail below, processor 30 collects information relating to tested electrode combinations, and stores the information in memory 32 for later retrieval and review by the clinician to facilitate identification of desirable electrode configurations. Neurostimulation therapy programs 40 created by the clinician may be stored in memory 32, and information identifying electrode configurations selected by the clinician to be utilized for one of programs 40 may be stored as part of the program within memory 32. Memory 32 may include any volatile, nonvolatile, fixed, removable, magnetic, optical, or electrical media, such as a RAM, ROM, CD-ROM, hard disk, removable magnetic disk, memory cards or sticks, NVRAM, EEPROM, flash memory, and the like.

Processor 30 controls IMD 14 to test selected individual electrodes 26 or electrode combinations, by controlling IMD 14 to deliver neurostimulation therapy to patient 12 via the selected individual electrodes 26 or electrode combinations via a telemetry circuit 41. Processor 30 may transmit programs 40 created by the user to IMD 14 via telemetry circuit 41, or to another programmer used by the patient to control delivery of neurostimulation therapy via input/output circuitry 42. I/O circuitry 42 may include transceivers for wireless communication, appropriate ports for wired communication or communication via removable electrical media, or appropriate drives for communication via removable magnetic or optical media.

Figure 4:
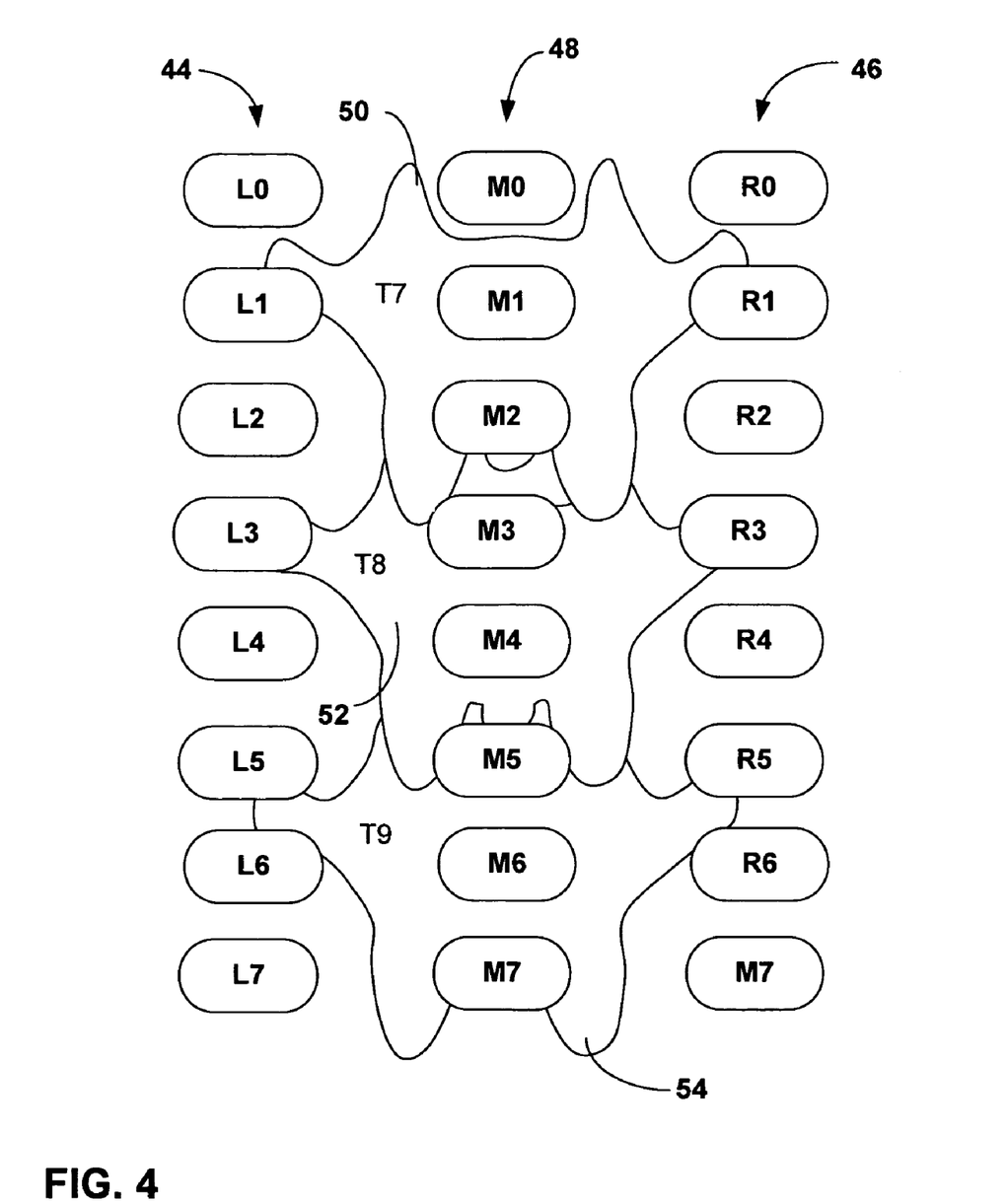
FIG. 4 is a diagram illustrating locations of configuration nodes and target region nodes used to form probability relationships in a Bayesian network structure.

FIG. 4 is a diagram illustrating locations of target region nodes 44, 46, 48 used to form probability relationships in a Bayesian network structure. Using the Bayesian network structure, programmer 20 provides suggestions on which parameter configurations are most likely to be efficacious given the results of tests already performed during a visit to a clinician. This is accomplished by capturing the causal relationships between different variables in the system, which can be represented by a graphical network structure. For each node 44, 46, 48 in the Bayesian network structure, a conditional probability table can be developed that specifies the probabilities associated with each state of that node given each state of each of its parent nodes, i.e., in the causally-related sense.

This Bayesian network structure, along with its probability tables, can then be used to infer the most likely states of nodes given observations made on other nodes. For instance, if electrode configuration 1 is rated highly by the patient (very efficacious) while electrode configuration 2 is rated poorly (no efficacy), the Bayesian network might infer that configuration 3 will be efficacious with a 70% probability while configuration 4 will be efficacious with only a 5% probability, in recognition of the causal relationship between those nodes. This kind of information can then be used to guide an optimization process by always selecting, as the next configuration for the clinician to try, the configuration that is most likely to yield efficacious results, e.g., in terms of symptom relief, coverage area relative to symptom area, and side effects. In this way, the number of observations that need be made to ensure a good outcome is reduced.

In practice, the structure and probabilities of a Bayesian network can be determined in one of two ways. If sufficient data is available, algorithms exist to learn the network directly from the data. Alternately, the network can be designed based upon the input and opinions of experts in the domain, i.e., experts in neurostimulation programming for a particular application such as spinal cord stimulation. As a specific example, consider the problem of selecting the optimum electrodes in a 2 by 8 lead electrode system for the treatment of pain. The following discussion describes the design and use of a Bayesian network useful for this problem. Although any combination (anodes, cathodes, and opens) of the sixteen electrodes 26 is conceivably possible, this example will consider only bipole pairs of electrodes 26.

Thus, a first set of variables for the Bayesian network will be selected to represent the observed or observable ratings of pairs of electrodes 26. In this example, each of these variables can have one of five states, e.g., '1' to '5', representing the subjective rating the patient gave to the therapeutic effects created by the configuration. A second set of variables will be selected to represent the underlying physiology. In order to capture the possibility that the pain is on the left, on the right, or in the center (transverse), three sets of target nodes 44, 46, 48 are used, as shown in FIG. 4. Each of these nodes can have one of two states (yes/no), representing whether the region is involved in the pain that is being treated. These nodes will be considered to have a causal relationship with the electrode pairs, i.e., an active physiological target region 'causes' an observed rating on an electrode pair.

FIG. 4 shows the mapping of these sets of nodes 44, 46, 48 to the underlying physiology of the T7, T8, and T8 vertebrae. Notably, in FIG. 4, sets of nodes 44, 46, 48 are applied in the context of spinal cord stimulation for purposes of illustration, but may be readily applicable to other types of neurostimulation. In FIG. 4, nodes L0–L8 represent target regions on the left, nodes M0–M8 represent target regions in the middle, and nodes R0–R8 represent target regions on the right. The target regions refer to areas in which neurostimulation energy can be directed, via implanted electrodes, to relieve symptoms. Neurostimulation is often thought to have a localized relationship with respect to the physiological structures that are being targeted. In the model shown in FIG. 4, this can be reflected by limiting the effect of an active target region to the electrode pairs in closest proximity, e.g., above left, left, below left, above mid, mid, below mid. Although FIG. 4 depicts the linking of adjacent electrode pairs, other techniques for representing the locality effect may be appropriate in some embodiments.

Figure 5:
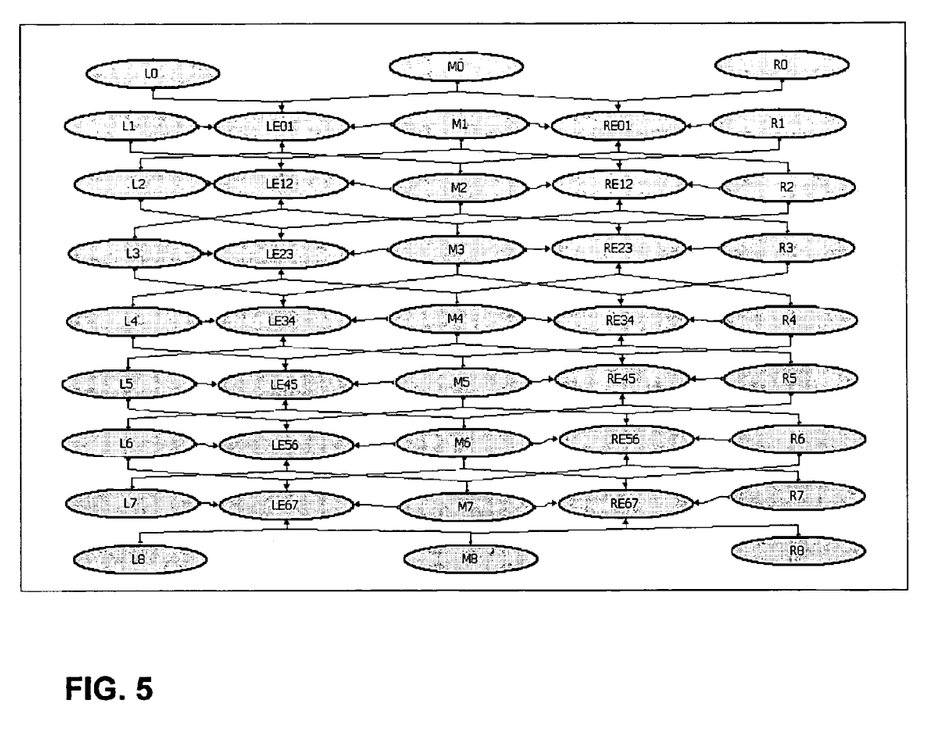
FIG. 5 is a diagram illustrating a Bayesian network structure showing configuration nodes, target region nodes, and associated connections.

FIG. 5 is a diagram illustrating a Bayesian network structure showing configuration nodes, target region nodes, and associated connections. In the example of FIG. 5, nodes LE01–LE67 and RE01–RE67 represent electrode pairs, and are referred to herein as configuration nodes. Nodes L0–L8, M0–M8 and R0–R8 in FIG. 5 are target region nodes representing target regions of the physiology, as also shown in FIG. 4. Target region nodes may also be referred to as physiology nodes. The configuration nodes and target region nodes are interconnected by a connection structure that represents causal relationships between the nodes. Probabilities for the nodes can be generated in a similar manner. If a node is rated highly in terms of efficacy, the probability of its neighbors being rated well is strong; if it is rated poorly, the probability of its neighbor being rated well is low.

Figure 6:
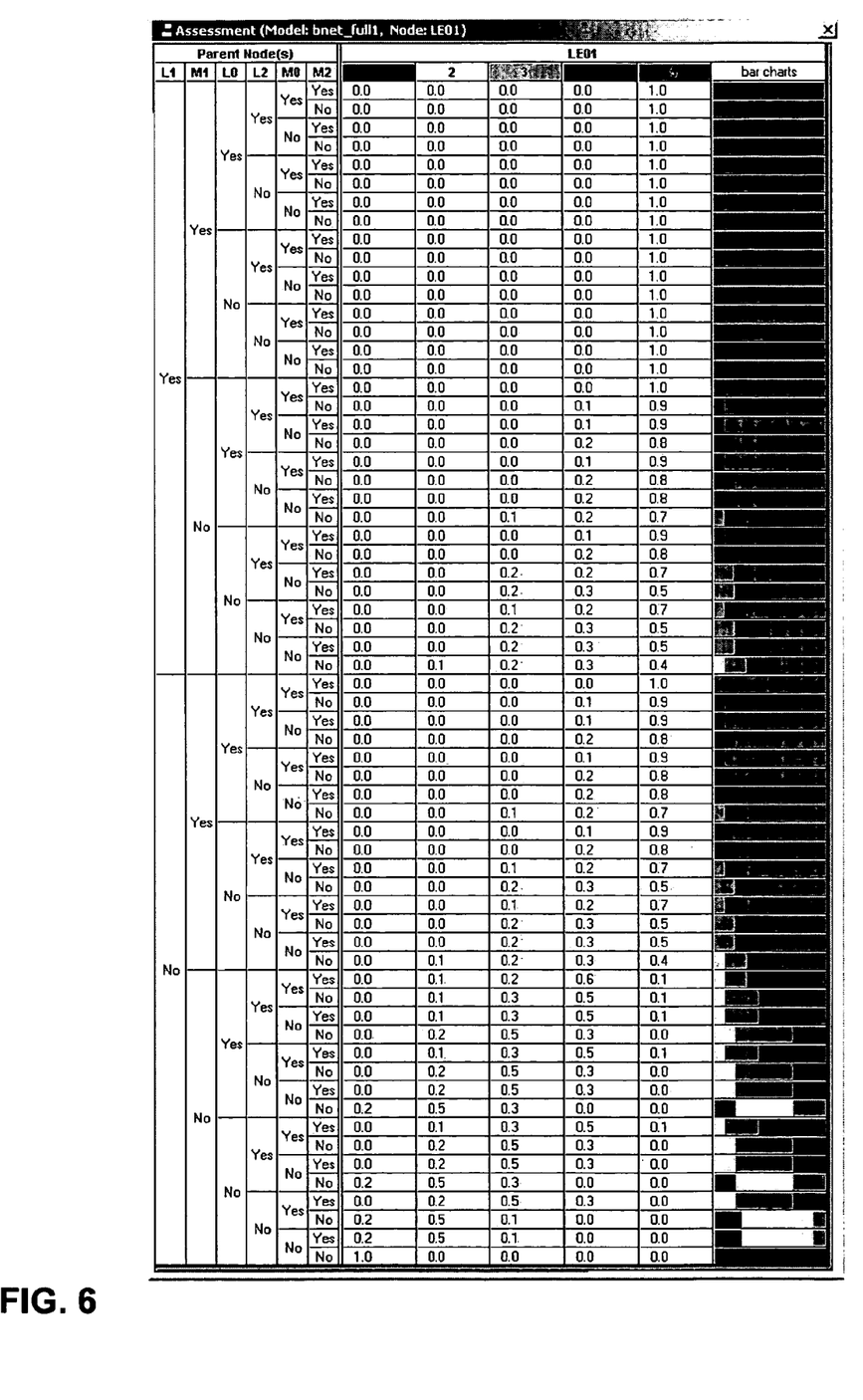
FIG. 6 is an exemplary probability table for a Bayesian network structure as shown in FIG. 5.

FIG. 6 is an exemplary probability table for a Bayesian network structure as shown in FIG. 5. The probability table of FIG. 6 represents a set of probabilities determined by experts in the neurostimulation domain, as it is used for the full Bayesian network. In execution of the electrode configuration search algorithm, this Bayesian network can be used to guide the selection of electrode pairs for the clinician to test. As an illustration, this process could follow an evaluation policy similar to the following:

1. Try the center electrode, left lead. (Arbitrary, default choice.)
2. Try the electrode pair associated with the most probable target zone, given the observation from the previous electrode configuration. If no probability is higher than a baseline probability, e.g., 0.5, widen the search by selection of pairs of electrodes with baseline probabilities, e.g., 0.5, nearest the center, alternating leads.
3. Repeat the process iteratively until a desired level of confidence is achieved, e.g., greater than 0.8, or until all probabilities are below a baseline, e.g., less than 0.5.

The probability table of FIG. 6 corresponds to configuration node LE01. With reference to FIG. 5, configuration node LE01 represents a combination of electrode L0 and electrode L1, e.g., an electrode pair. Although electrode pairs are illustrated in FIG. 6, some configuration nodes may represent combinations of more than two electrodes. Electrodes L0 and L1 are the first and second electrodes on the left lead in the spinal cord stimulation example involving left and right leads with multiple electrodes. Hence, configuration node LE01 represents application of neurostimulation energy between electrodes L0 and L1.

In the probability table of FIG. 6, configuration node LE01 is rated in terms of efficacy for each target node L1, M1, L0, L2, M0, M2. A probability table exists for each observable node (each electrode configuration node) that relates the possible observed states of the configuration node to the states of its casually linked target region nodes (the physiology nodes). These tables can be learned from a set of data, via statistical analysis of the relationships between variables, or specified by experts in the domain. FIG. 6 shows a representative example of such a table for a sample system being considered. Each row in the table of FIG. 6 shows the probabilities for the electrode configuration node based on one set of conditions of the target region (physiology) nodes. For example, the first row states that the probability for the LE01 configuration node to be rated a '5' is 1.0 given that all of its adjacent target region nodes (L1, M1, L0, L2, M0, M2) are of interest, i.e., therapeutically relevant in that the stimulation of the corresponding regions produces clinically useful results.

These probabilities in the table of FIG. 6 can be used to make inferences as to the likely values of target nodes based on observations. For example, knowing that a configuration node has been observed with a given value, e.g., that LE01=3, allows the system to calculate a distribution for the causative nodes (L1, M1, etc.). Knowing several observations allows the system to make more generalized calculations about the likely states of the target region (physiological) nodes, which are considered causative nodes. In turn, knowing the likely states of the causative, physiological nodes allows the system to make recommendations about the next observation to make.

As an example, the user might observe several electrode configuration nodes. Based on these observations, the network can calculate or infer the likely, i.e., probable, states of the causative, physiological nodes. It might then suggest, as a next observation, an as of yet unobserved electrode node close to the physiological node with the highest inferred probability. In this manner, the clinician is guided to electrode configurations that are more likely to yield efficacious results for the patient, reducing clinician time and effort, and possibly yield optimal or near-optimal results that otherwise might not be achieved. Similar results may be obtained by application of a Bayesian network structure for other parameters in a parameter configuration, such as amplitude, pulse width and pulse rate.

FIG. 7 is a diagram of a sample search execution sequence for a Bayesian network structure as depicted in FIGS. 4–6. To illustrate this process, the table of FIG. 7 shows the execution of an example evaluation policy on a set of test data. FIG. 7 shows the probability values (Yes/No) for each of the target region nodes for each of five iteration steps. At the bottom of the table are the evidence values that inform each column above, i.e., the observation that led to the probabilities represented in the column. One of the nodes (labeled "T") shows the terminating probability (per a policy that requires probability P>0.8).

One exemplary execution of the search algorithm, with reference to FIG. 7, can described by the following operations:

1. Evaluate left lead, middle electrode (LE34=1)
2. Evaluate right lead, middle electrode (RE34=3)
3. Right lead is better. Expand search on right lead (RE23=2)
4. Expand search again (RE45=4)
5. Expand search again (RE12=1)
6. Expand search again (RE56=5)
7. Discovered good location. Extend search one further (RE67=4)
8. Extend search across (transverse) (LE56=2)
9. Terminate—RE56 is optimum Although this example shows the use of a network for optimization of electrodes, it can be readily extended to include other stimulation parameters of interest as well, such as voltage and current amplitudes, frequency, pulse width, pulse rate, duration, and the like. The search capability can be implemented as a feature in an implantable device programmer 20. Following the programming of a configuration of parameters, the programmer 20 may prompt for a rating of the efficacy of that configuration. This rating could be solicited from the patient by the clinician, or entered directly by the patient. In general, efficacy refers to the balance between therapeutic benefit and undesirable side effects. As examples, efficacy ratings can be obtained by verbal feedback from the patient concerning therapeutic benefit and side effects, marking of a pain/parasthesia map, objective measurement using pain rating scales, quantification of side effects, a combination of the forgoing, or other observation techniques. The programmer 20 then uses this rating with the network model appropriate for the therapy and device type to infer the best next step. This step would then be suggested to the clinician by the programmer interface.

Figure 8:
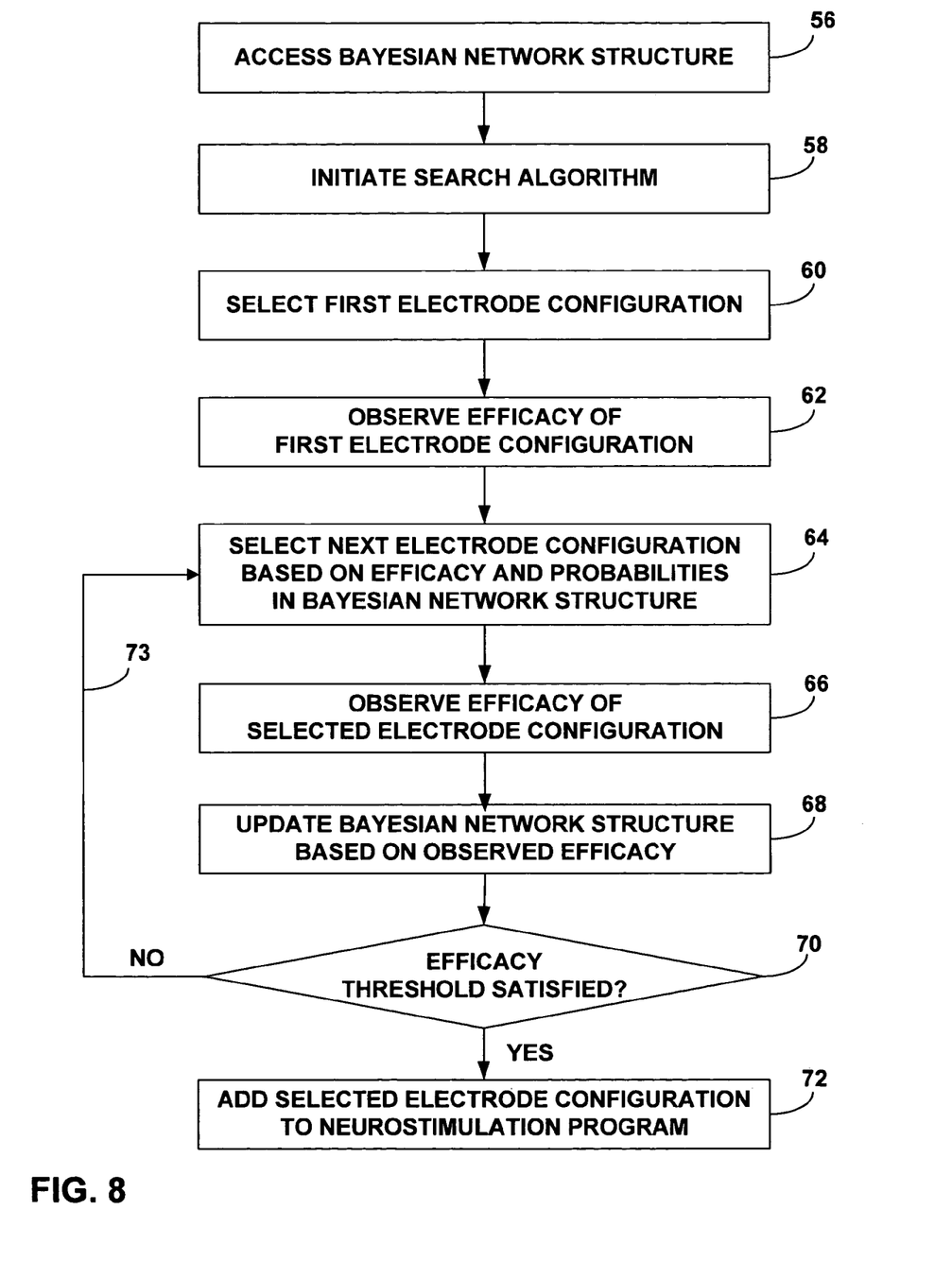
FIG. 8 is a flow diagram illustrating a search algorithm that is executable by a programmer to select parameter configurations.

FIG. 8 is a flow diagram illustrating a search algorithm that is executable by a programmer to select electrode configurations. As shown in FIG. 8, the algorithm involves accessing the Bayesian network structure (56), initiating the search algorithm (58), selecting a first electrode configuration (60), and observing the efficacy of the first electrode configuration (62). The efficacy may be rated positively in terms of pain relief or other therapeutic benefit, and negatively in terms of side effects of the therapy. Based on the observed efficacy and probabilities for causal relationships represented in the Bayesian network structure, the next electrode configuration is selected (64). The algorithm then involves observing efficacy of that newly selected electrode configuration (66) and updating the Bayesian network structure to reflect the observed efficacy (68). If an applicable efficacy threshold is satisfied (70), the algorithm may terminate and add the selected electrode configuration to a stored neurostimulation program or create a new neurostimulation program (72). If the threshold is not satisfied, the process may repeat iteratively (73) until the threshold is satisfied or the clinician elects to manually terminate the algorithm. Although FIG. 8 focuses on electrode configurations, the techniques generally depicted therein may be adapted for other configuration parameters.

Figure 9:
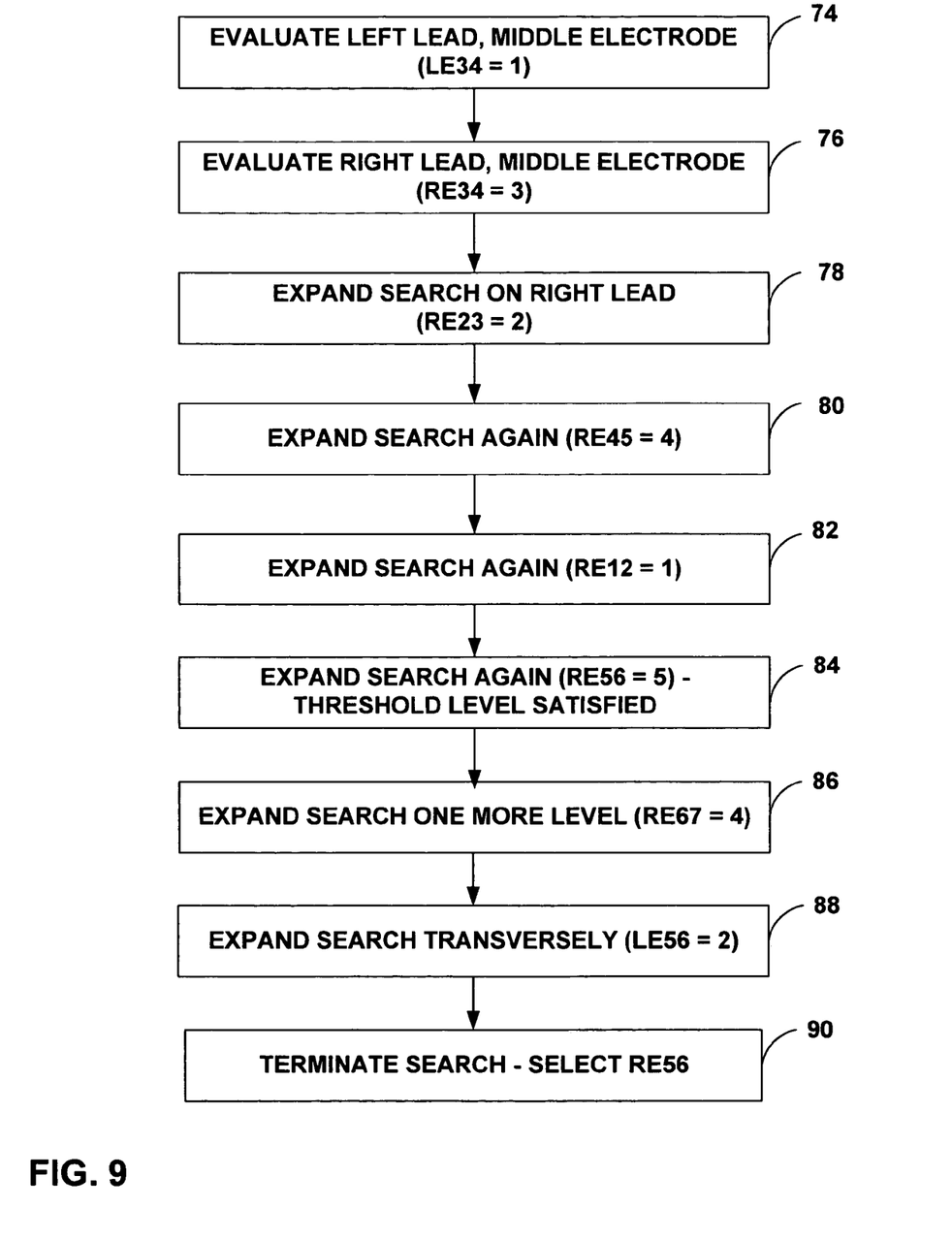
FIG. 9 is another flow diagram illustrating a sample search execution sequence.

FIG. 9 is another flow diagram illustrating a sample search execution sequence. More specifically, FIG. 9 illustrates a particular sequence as described above with respect to FIG. 7. As shown in FIG. 9, the sequence involves evaluating left lead, middle electrode (LE34=1) (74), evaluating right lead, middle electrode (RE34=3) (76), upon finding that the right lead is better, expanding the search on the right lead (RE23=2) (78). The, the search is expanded again (RE45=4) (80), and again (RE12=1) (82), and again (RE56=5) (84). Once a good location is discovered, the search may be extended one further level (RE67=4) (86), followed by a transverse search (LE56=2) (88). Then, the search is terminated when it is found that RE56 is better and determined to be optimum (90).

If the clinician stops the search before all possible combinations of electrodes 26 have been tested, programmer 20 may create a bracket of untested combinations that the clinician may elect to include in neurostimulation therapy programs. The bracket may consist of any number of electrode combinations, and may comprise the next n combinations that would have been tested according to the electrode combination search algorithm. By providing the clinician with a bracket, programmer 20 may allow clinician to spend less time searching for desirable electrode combinations in a subsequent programming session. Specifically, the programs created using the bracket combinations may enable desirable neurostimulation therapy similar to that provided in a program created with the most recently tested combination, and may be provided to patient 12 so that patient 12 can experiment with the bracket programs outside of the clinic.

As described herein, programmer 20 controls IMD 14 to test electrode configurations by controlling IMD 14 to deliver neurostimulation therapy via combinations of electrodes. In addition, programmer 20 may be configured to facilitate a search for other optimum therapy parameters, as described herein. For example, the clinician or programmer 20 may select desired starting points for pulse amplitude, rate and pulse width for each electrode configuration, and programmer 20 may ramp the amplitude from the starting point at a first rate of amplitude increase using similar Bayesian network techniques. Programmer 20 may increase the amplitude in, for example, a linear or step-wise fashion. In some embodiments, the clinician or patient 12 may control the rate of amplitude increase. The clinician or patient 12 stops the ramping of the amplitude when the stimulation causes discomfort, or other undesirable side effects.

Programmer 20 may reduce the amplitude at the time the ramp is stopped by some amount, e.g., a percentage, and ramps the amplitude again in order to allow the clinician and/or patient 12 to identify the amplitude that provides the best neurostimulation therapy. This second time, programmer 20 may ramp the amplitude at a slower rate of amplitude increase in order to facilitate identification of the point where best neurostimulation is achieved. Again, in some embodiments, the clinician or patient 12 may control the amplitude.

Programmer 20 stores the amplitude at the time when the best neurostimulation therapy is indicated by the clinician and/or patient 12, and rating information for the electrode configuration. The clinician and/or patient 12 may provide efficacy rating information, e.g., a numerical value for one or more metrics for rating the combination, which relates to the efficacy enabled by the combination or the side effects resulting from use of the combination, or both. Again, efficacy ratings can be obtained by verbal feedback from the patient concerning therapeutic benefit and side effects, marking of a pain/parasthesia map, objective measurement using pain rating scales, quantification of side effects, a combination of the forgoing, or other observation techniques.

The clinician may use rating information and/or the amplitude values stored for each tested combination to identify desirable electrode configurations. The configurations and their associated information and values may be presented in a list that may be ordered according to the information, the values, or a combination of the two. The amplitude value may, for example, be used to distinguish between tested combinations with similar ratings based on the power that must be consumed in order for each combination to enable desirable neurostimulation therapy.

Various embodiments of the invention have been described. However, one skilled in the art will appreciate that various additions and modifications can be made to these embodiments without departing from the scope of the invention. The invention may be generally applicable to any programming optimization problem in which the feedback from a configuration is available relatively quickly and within the context of the clinical programming environment. This includes the stimulation therapies for pain and movement disorders and may include other stimulation-based therapies as well.

For example, although programmer 20 has been described herein as a hand-held computing device, programmer 20 may take the form of any type of computing device, such as a laptop or desktop computer, may access resources, such as memory 54, via a computer network, such as a LAN, WAN, or the World Wide Web. Further, programmer 20 may include a plurality of computing devices, which may communicate to provide the functionality ascribed to programmer 20 herein via a computer network.

Although described herein as associated with and interacting with a clinician, i.e., a clinician programmer, programmer 20 may be associated with patient 12, i.e., a patient programmer. Also, other users, such as technicians or other medical personnel may use programmer 20. In some embodiments, patient 12 may simply interact with programmer 20 in place of the clinician for some or all of the electrode combination identification process. In other embodiments, patient 12 may perform parts of the configuration identification process without being supervised by the clinician, e.g., away from the clinic, using a patient programmer. In addition, the invention may be useful for a wide variety of neurostimulation contexts including spinal cord stimulation, deep brain stimulation, gastric stimulation, pelvic stimulation, sacral stimulation, and others. These and other embodiments are within the scope of the following claims.

The invention claimed is:

1. A method comprising:
   selecting a first parameter configuration for a neurostimulator;
   observing efficacy of the first parameter configuration; and
   selecting a second parameter configuration for the neurostimulator based on the observed efficacy of the first parameter configuration and a Bayesian network structure relating additional parameter configurations according to probability of efficacy.

2. The method of claim 1, wherein the parameter configurations include electrode configurations, each of the electrode configurations defining a combination of two or more electrodes for delivery of neurostimulation energy.

3. The method of claim 2, wherein each of the electrode configurations defines polarities for electrodes in the combination.

4. The method of claim 2, wherein the electrodes are associated with different target regions within a body of a patient.

5. The method of claim 2, wherein the electrodes are carried by two or more implanted leads.

6. The method of claim 5, wherein the implanted leads are implanted proximate a portion of a spine of a patient.

7. The method of claim 2, wherein the Bayesian network structure defines a plurality of configuration nodes representing different electrode configurations, a plurality of target region nodes representing target regions within a body of a patient, and an efficacy probability relationship among the configuration nodes and the target regions.

8. The method of claim 7, further comprising iteratively selecting additional electrode configurations for the neurostimulator based on observed efficacy of preceding electrode configurations and the Bayesian network structure.

9. The method of claim 8, further comprising terminating the iterative selection of the additional electrode configurations when one or more termination criteria are satisfied.

10. The method of claim 9, wherein the termination criteria include selection of one of the electrode configurations with an observed efficacy that satisfies a threshold efficacy.

11. The method of claim 7, further comprising observing efficacy of the electrode configurations in each of the target regions, and representing the observed efficacy in the configuration nodes and the target region nodes of the Bayesian network structure.

12. The method of claim 2, further comprising:
   iteratively selecting additional electrode configurations for the neurostimulator based on observed efficacy of preceding electrode configurations and the Bayesian network structure;
   terminating the iterative selection of the additional electrode configurations at a final electrode configuration when one or more termination criteria are satisfied; and
   programming the neurostimulator to employ the final electrode configuration in delivery of neurostimulation therapy.

13. The method of claim 12, wherein the neurostimulator is a spinal cord stimulator, and the final electrode configuration includes electrodes deployed on one more implanted spinal leads.

14. The method of claim 12, wherein the final electrode configuration defines a combination of two electrodes from a set of at least eight electrodes.

15. The method of claim 2, further comprising:
   iteratively selecting additional electrode configurations for the neurostimulator based on observed efficacies of preceding electrode configurations and the Bayesian network structure; and
   modifying probability relationships represented by the Bayesian network structure based on the observed efficacies.

16. The method of claim 1, wherein selecting the first and second parameter configurations includes suggesting the first and second parameter configurations to a clinician.

17. The method of claim 1, wherein observing efficacy includes receiving user input indicating observed efficacy.

18. A computer-readable medium comprising instructions to cause a processor to:
   select a first parameter configuration for a neurostimulator;
   observe efficacy of the first parameter configuration; and
   select a second parameter configuration for the neurostimulator based on the observed efficacy of the first parameter configuration and a Bayesian network structure relating additional parameter configurations according to probability of efficacy.

19. The computer-readable medium of claim 18, wherein the parameter configurations include electrode configurations, each of the electrode configurations defining a combination of two or more electrodes for delivery of neurostimulation energy.

20. The computer-readable medium of claim 19, wherein each of the electrode configurations defines polarities for electrodes in the combination.

21. The computer-readable medium of claim 19, wherein the electrodes are associated with different target regions within a body of a patient.

22. The computer-readable medium of claim 19, wherein the electrodes are carried by two or more implanted leads.

23. The computer-readable medium of claim 19, wherein the implanted leads are implanted proximate a portion of a spine of a patient.

24. The computer-readable medium of claim 19, wherein the Bayesian network structure defines a plurality of configuration nodes representing different electrode configurations, a plurality of target region nodes representing target regions within a body of a patient, and an efficacy probability relationship among the configuration nodes and the target regions.

25. The computer-readable medium of claim 24, wherein the instructions cause the processor to iteratively select additional electrode configurations for the neurostimulator based on observed efficacy of preceding electrode configurations and the Bayesian network structure.

26. The computer-readable medium of claim 25, wherein the instructions cause the processor to terminate the iterative selection of the additional electrode configurations when one or more termination criteria are satisfied.

27. The computer-readable medium of claim 26, wherein the termination criteria include selection of one of the electrode configurations with an observed efficacy that satisfies a threshold efficacy.

28. The computer-readable medium of claim 24, wherein the instructions cause the processor to observe efficacy of the electrode configurations in each of the target regions, and represent the observed efficacy in the configuration nodes and the target region nodes of the Bayesian network structure.

29. The computer-readable medium of claim 19, wherein the instructions cause the processor to:
iteratively select additional electrode configurations for the neurostimulator based on observed efficacy of preceding electrode configurations and the Bayesian network structure;
terminate the iterative selection of the additional electrode configurations at a final electrode configuration when one or more termination criteria are satisfied; and
program the neurostimulator to employ the final electrode configuration in delivery of neurostimulation therapy.

30. The computer-readable medium of claim 29, wherein the neurostimulator is a spinal cord stimulator, and the final electrode configuration includes electrodes deployed on one more implanted spinal leads.

31. The computer-readable medium of claim 30, wherein the final electrode configuration defines a combination of two electrodes from a set of at least eight electrodes.

32. The computer-readable medium of claim 19, wherein the instructions cause the processor to:
iteratively select additional electrode configurations for the neurostimulator based on observed efficacies of preceding electrode configurations and the Bayesian network structure; and
modify probability relationships represented by the Bayesian network structure based on the observed efficacies.

33. The computer-readable medium of claim 18, wherein the instructions cause the processor to select the first and second parameter configurations by suggesting the first and second parameter configurations to a clinician.

34. The computer-readable medium of claim 18, wherein the instructions cause the processor to observe efficacy includes by receiving user input indicating observed efficacy.

35. A device comprising a processor programmed to:
select a first parameter configuration for a neurostimulator;
observe efficacy of the first parameter configuration; and
select a second parameter configuration for the neurostimulator based on the observed efficacy of the first parameter configuration and a Bayesian network structure relating additional parameter configurations according to probability of efficacy.

36. The device of claim 35, wherein the parameter configurations include electrode configurations, each of the electrode configurations defining a combination of two or more electrodes for delivery of neurostimulation energy.

37. The device of claim 36, wherein each of the electrode configurations defines polarities for electrodes in the combination.

38. The device of claim 36, wherein the electrodes are associated with different target regions within a body of a patient.

39. The device of claim 36, wherein the electrodes are carried by two or more implanted leads.

40. The device of claim 36, wherein the implanted leads are implanted proximate a portion of a spine of a patient.

41. The device of claim 36, wherein the Bayesian network structure defines a plurality of configuration nodes representing different electrode configurations, a plurality of target region nodes representing target regions within a body of a patient, and an efficacy probability relationship among the configuration nodes and the target regions.

42. The device of claim 41, wherein the processor iteratively selects additional electrode configurations for the neurostimulator based on observed efficacy of preceding electrode configurations and the Bayesian network structure.

43. The device of claim 42, wherein the processor terminates the iterative selection of the additional electrode configurations when one or more termination criteria are satisfied.

44. The device of claim 43, wherein the termination criteria include selection of one of the electrode configurations with an observed efficacy that satisfies a threshold efficacy.

45. The device of claim 41, wherein the processor observes efficacy of the electrode configurations in each of the target regions, and represents the observed efficacy in the configuration nodes and the target region nodes of the Bayesian network structure.

46. The device of claim 36, wherein the processor:
iteratively selects additional electrode configurations for the neurostimulator based on observed efficacy of preceding electrode configurations and the Bayesian network structure;
terminates the iterative selection of the additional electrode configurations at a final electrode configuration when one or more termination criteria are satisfied; and
programs the neurostimulator to employ the final electrode configuration in delivery of neurostimulation therapy.

47. The device of claim 46, wherein the neurostimulator is a spinal cord stimulator, and the final electrode configuration includes electrodes deployed on one more implanted spinal leads.

48. The device of claim 47, wherein the final electrode configuration defines a combination of two electrodes from a set of at least eight electrodes.

49. The device of claim 36, wherein the processor:
iteratively selects additional electrode configurations for the neurostimulator based on observed efficacies of preceding electrode configurations and the Bayesian network structure; and
modifies probability relationships represented by the Bayesian network structure based on the observed efficacies.

50. The device of claim 35, wherein the processor selects the first and second parameter configurations by suggesting the first and second parameter configurations to a clinician.

51. The device of claim 35, wherein the processor observes efficacy by receiving user input indicating observed efficacy.

* * * * *